United States Patent [19]
Baranowski

[11] Patent Number: 5,944,683
[45] Date of Patent: Aug. 31, 1999

[54] PROTECTION AND TREATMENT DEVICE FOR ANKLE, HEEL AND ELBOW PROMINENCES

[76] Inventor: Edwin M. Baranowski, 75 Marrus Dr., Gahanna, Ohio 43230

[21] Appl. No.: 09/256,277

[22] Filed: Feb. 23, 1999

Related U.S. Application Data

[63] Continuation of application No. 08/608,826, Feb. 29, 1996, Pat. No. 5,882,324.

[51] Int. Cl.⁶ .................................................. A61F 13/00
[52] U.S. Cl. ............................. 602/65; 602/46; 602/48; 602/54; 128/889; 128/892; 128/894
[58] Field of Search ................... 135/65, 68, 70, 135/86; 128/888, 889, 890, 892, 893, 894; 602/41–48, 52–59

[56] References Cited

U.S. PATENT DOCUMENTS

| | | | |
|---|---|---|---|
| 2,712,311 | 7/1955 | Scholl | 128/894 |
| 4,917,112 | 4/1990 | Kalt | 128/888 X |
| 5,086,763 | 2/1992 | Hathman | 128/888 X |
| 5,882,324 | 3/1999 | Baranowsky | 128/892 X |

*Primary Examiner*—Richard J. Apley
*Assistant Examiner*—Kim M. Lee

[57] ABSTRACT

A protection and treatment device for ankle, heel and elbow prominences of bed ridden patients in the form of a topically applied pressure resilient cushion adapted to be positioned on the skin adjacent the bony prominence in which a pad having a relatively flat surface conformable to the skin area at which it is applied contains a recess essentially to embrace the bony prominence and includes a perimeter section around the recess that abuts the skin around the bony prominence and supports the cushion against the body tissue adjacent the prominence. The cushion includes multiple sections having differing cross-sections and may be provided in adhesive and medicated configurations maintained in place by a.

2 Claims, 2 Drawing Sheets

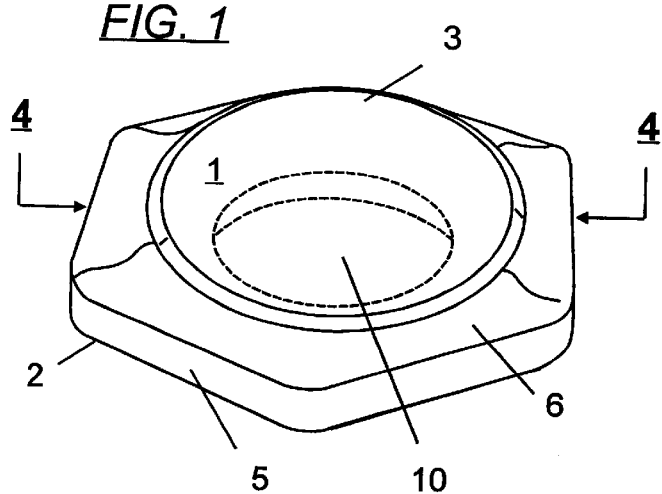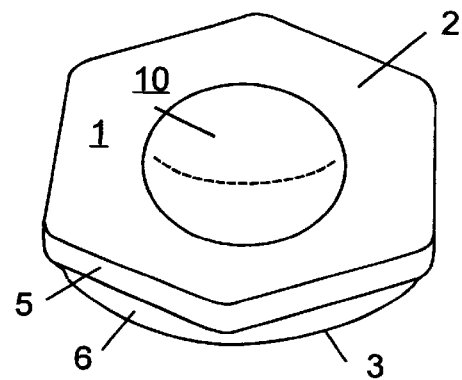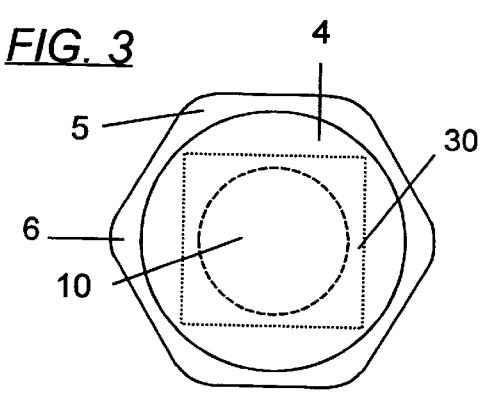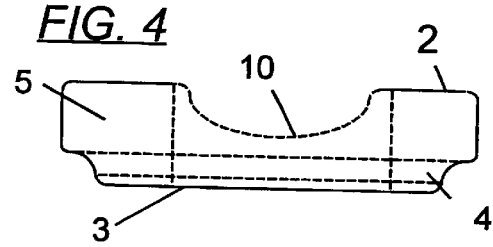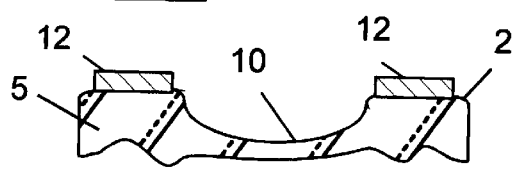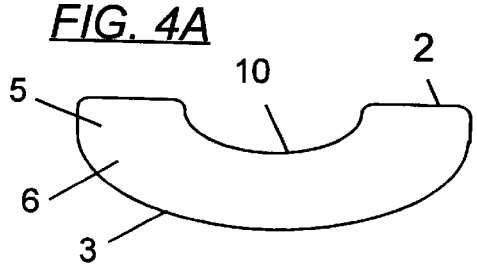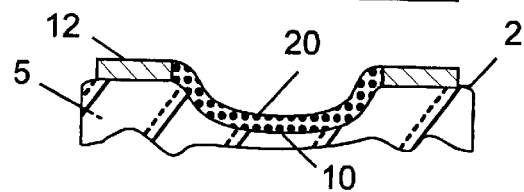

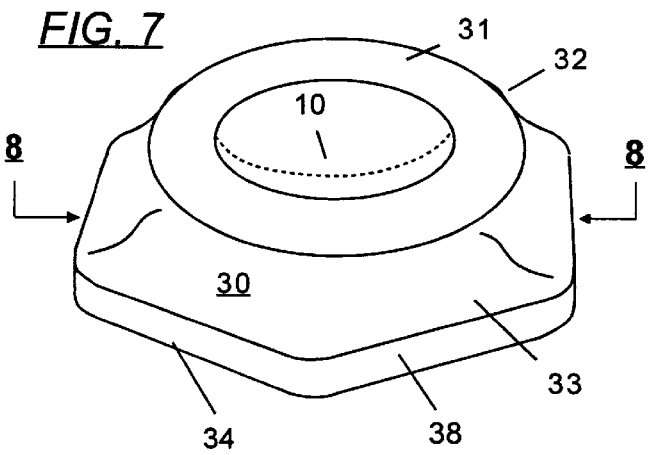
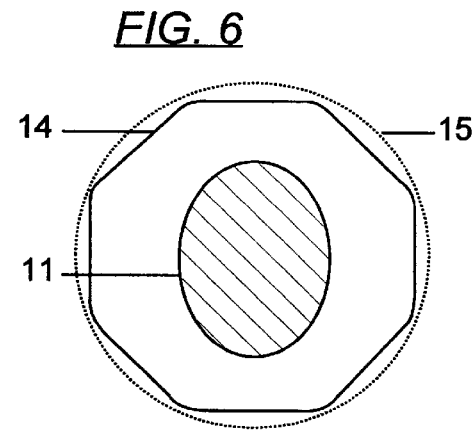
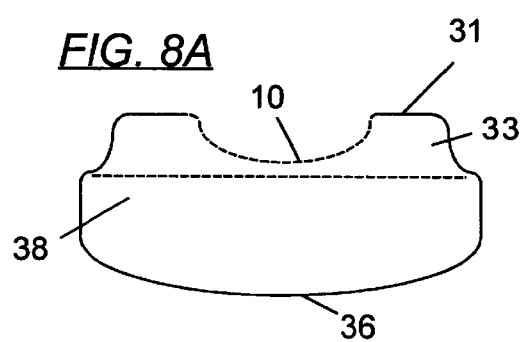
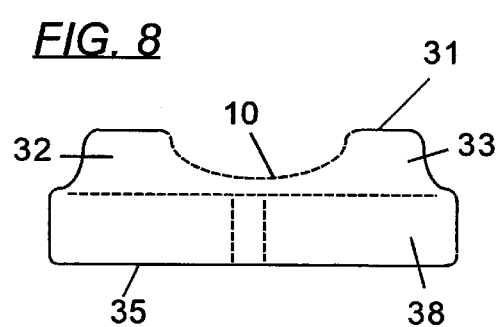
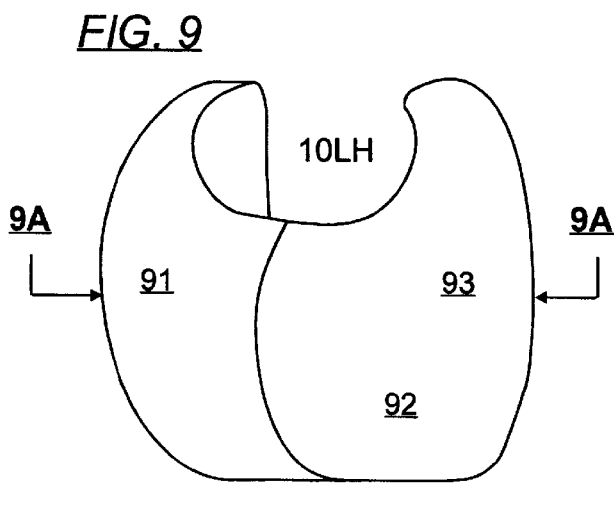
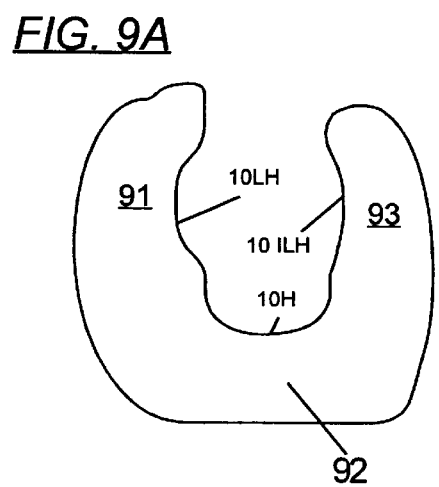

PROTECTION AND TREATMENT DEVICE FOR ANKLE, HEEL AND ELBOW PROMINENCES

RELATED APPLICATION

This is a continuation of my original application Ser. No. 08/608,826, filed Feb. 29, 1996 for Protection and Treatment Device for Ankle, Heel and Elbow Prominences, now allowed and to be issued as U.S. Pat. No. 5,882,324.

FIELD OF THE INVENTION

This invention relates to a device for protecting skeletal bony prominences from undue pressure that causes skin breakdowns, dermal ulcers and other adverse health conditions and for assisting in the treatment of such conditions.

BACKGROUND OF THE INVENTION

Dermal breakdown, bedsores and skin ulcers are serious and difficult to treat medical problems for long term care patients, and other bed ridden patients having reduced sensation or circulation as a result of diabetes, spinal cord injury, stroke, circulatory problems and other conditions. Skin breakdowns typically occur secondarily to treatment for some other condition and result after a patient is confined in bed when bony prominences, such as ankles, heels and elbows are exposed to persistent pressure as a result of a stationary position. Once a breakdown occurs and/or a sore develops, treatment is necessary. Care for the wound is extended and long term, regardless of the patient's primary health problem. Complications such as infections and abscesses may develop in what superficially appears to be a small affected skin area. These complications in turn adversely affect a patient's overall condition and/or the duration of confinement and need for care in a hospital, care facility, home, or the like. Medical devices in the form of a control gel formula dressing such as DuoDERM®, a product of Bristol-Myers Squibb Canada, Inc., Montreal, Québec, Canada (U.S. Pat. No. 4,551,490); a membrane dressing such as Ferris PolyMem™, a product of Ferris Mfg. Corp., Burr Ridge, Ill. (U.S. Pat. Nos. 4,884,563, 5,064,653 and 5,065,752); a hydrophilic polyurethane dressing such as Allevyn™, a product of Smith+Nephew Medical Limited, Hull, England, have all found acceptance in the treatment of dermal ulcers, pressure sores and wounds. A characteristic common to the foregoing dressings is that they are typically provided as pads about 0.25 cm thick in sizes ranging from 5 cm×5 cm to 20 cm×20 cm and are cut to shape to surround the wound about 1.5 to 2.0 cm about its periphery. These dressings are either self-adhesive or are secured to the wound location with an adhesive tape or bandage. Preventative efforts to prevent breakdowns from occurring include periodic repositioning of a patient and the use of a pillow or gel cushion at a pressure point. In the case of feet, colloquially referred to "space boots" are often used that consist of a foam web or sheet about up to approximately 2.5 cm thick that wrap around and cover each foot of a patient.

OBJECTS AND SUMMARY OF THE INVENTION

An object of the invention is to reduce the incidence of skin breakdowns and sores occurring at bony prominences of bed ridden patients by providing a disposable device for attachment at and proximate to bony prominences. It is a further object to provide a treatment device for breakdowns and sores as an adjunct to the use of existing dressings. The design of the device recognizes that even though a dermal breakdown is being treated with a dressing, the physical location of the breakdown at the dressing site should be protected from pressure. There exists a need for a device (1) that protects a bony prominence to prevent breakdown and (2) that supplements the protective character of a dressing when a breakdown is being treated. Thus, it is also an object to facilitate means for the application of pressure reducing devices at the vulnerable body locations at which breakdowns occur during the period of treatment. It is yet an object to provide an improvement over foam "space boots" applied to patients' feet, extended gel pads and pillows placed at bed locations and the like that are conventionally used. The device is topically applied and provides a fixed and focused protection at the bony prominences of the body that are most subject to breakdown. The invention is understood more readily by reference to the following description of the preferred embodiment, taken in conjunction with the drawings in which:

BRIEF DESCRIPTION OF THE DRAWINGS

FIG. 1 is a top perspective view of a device.

FIG. 2 is a bottom perspective view.

FIG. 3 is a plan view.

FIG. 4 shows a side view in cross-section through section 4—4 of FIG. 1.

FIG. 4A is an alternate cross-section for the device of FIG. 1.

FIG. 5A shows a shows a device with an adhesive surface for attachment to the skin.

FIG. 5B shows a shows an adhesive device combined with a treatment pad.

FIG. 6 shows an alternate shaped device useful with non-circular prominences such as elbows.

FIG. 7 shows an alternate shaped device.

FIG. 8 shows a side view in cross-section through section 8—8 of FIG. 7.

FIG. 8A shows a device with an alternate rounded surface on the side of the device opposite the side intended to face the skin.

FIG. 9 shows a heel and ankle cushion cup formed in accordance with the invention.

FIG. 9A is a cross-section through section 9A—9A of FIG. 9 also showing the cup with a foot inserted.

DESCRIPTION OF THE PREFERRED EMBODIMENT

The device depicted in FIG. 1 is essentially a cushion 1 formed of a closed cell foam (such as a polyurethane Temper Foam (Temper Foam is used in a wheelchair seat cushion sold by Kees-Goebel in Cincinnati, Ohio)) having a resilience with respect to pressure, and being resistant to compression. The cushion should have a density as measured by indentation load deflection appropriate to the weight of the body part supported and the surface area affected. Temper Foam from a wheelchair seat cushion having a resiliency characteristic appropriate for the sitting weight of a presenting patient is satisfactory in the preparation of the devices described herein that are useful with limbs of the same patient. Such types of resilient cushioning foams are known; appropriately configured air, gel and water cushions having comparable resilience characteristics that are also used in physiological environments may be substituted. The device is a protector for soft body tissue adjacent bony body prominences such as heels, ankles and elbows and comprises a pressure resilient cushion adapted to be topically applied and positioned on the skin adjacent the bony prominence. In brief, the resilient cushion includes a pad for facing the body skin. The pad has a relatively flat surface conformable to the skin area at which it is applied and contains an outer perimeter section and a recess therein sized essentially to embrace and receive therein the bony prominence. The recess is formed in a first surface section for abutting the skin at the bony prominence. The first section extends to an upper section having a cross-section differing from that of the first section. The first section and the upper section are intrinsically joined by an intermediate section connecting the sections.

In the device of FIG. 1, the device 1, on the side 2 intended to face the body skin, includes a relatively flat surface containing the recess therein 10 (shown in phantom) sized essentially to embrace a body prominence such as an ankle, elbow or heel. Transitions from the flat surface into the recess should be smoothly curved to follow body contours. The device has first thickness section 5 that abuts the skin and the first section tapers upwardly to upper section 3. The sections of the FIG. 1 device are differently shaped. In the example of FIG. 1, skin abutting section 5 extending from side 2 is hexagonal, both forming a platform on the skin and having opposite parallel side edges that assist in handling, placement and securing the device at the proper body location. The skin abutting section supports the cushion. With a convex ankle of approximately 3.5 cm in diameter nominally, the concentric section of the surface extending beyond the diameter of the recess extends another approximately 2 cm to 5 cm from the concave recess 10 to provide a support platform for the cushion. Similar size relationships for heel and elbow devices are evident. The upper section 3 is shown as circular and cushions the prominence, but as the section 3 is in contact with a bed surface, the section shape and edges are rounded or beveled to reduce friction and to permit movement in several directions. A straight or sharper edge would have a tendency to "catch" on a bed sheet and inhibit movement. A shoulder portion 6 of the device provides a transition from the skin facing pad section 5 to upper section 3 and as shown as 6 in FIG. 1 is in the form of a curvilinear ogee in cross-section. A view of the obverse side of the device of FIG. 1 is shown in FIG. 2. A cross-section of the device of FIG. 1 is shown in FIG. 4.

FIG. 3 is a top plan view of the device, showing concentrically positioned sections, lower pad skin facing section 5, upper section 3, shoulder section 6 and prominence embracing recess 10. An optional cut-out 30, as used in an alternative configuration shown in FIG. 5B, may be included to maintain a wound dressing 20 therein at the site of the wound. Preferably, a dressing cut-out is about 0.1 cm to 0.15 cm or more deep in the pad and square in shape to accommodate to existing rectangular shapes of medicated dressings such as Allevyn™ hydrophilic polyurethane, Ferris PolyMem™ membrane dressing, DuoDERM® control gel formula, referred to above, and conventional gauze pads and sponges. More simply, the size and shape of the recess may be inherently adapted for use with a provided dressing and/or the device and sterile dressing may be provided as a single unit. In FIG. 5A and FIG. 5B, the device is shown in cross-section also to include thereon on skin facing side 2 a pressure sensitive adhesive layer for bonding the device at the wound site. Such an intrinsic adhesive layer may be of the type used with DuoDERM® (described in U.S. Pat. No. 4,551,490) or adhesives used conventionally with medical bandages.

FIG. 6 shows a plan view of an alternate shaped device useful with an elbow having an elongated recess 11 in the first section gradually tapering to a depth of about 1.5 cm in a shape that cups the elbow protrusion. Alternative hexagonal 14 and circular or elliptical 15 pad sections are shown.

The devices are maintained in place by conventional dressing tape, or by a sock or sleeve at the ankle, heel or elbow affected, or by both.

An alternate shaped device is shown in FIG. 7 and in cross-section in FIG. 8. This alternate device 30 in the example is also formed of a resilient closed cell foam. The device is reversed in orientation from the pad of FIG. 1 such that the pad expands in cross-section from the skin facing surface having the recess indentation to the outer facing surface to provide a support platform therefor. Such a pyramid type of shape is useful as a heel or ankle protector where a larger surface area supports a weightier prominence. In FIG. 7, the flat face side 31, on the section 32 intended to face the body skin, is a relatively flat surface containing the recess 10 for embracing the prominence. Two sections form the device, upper section 32 and lower section 38 are joined by shoulder section 33. The device terminates at an opposite side 34, shown as flat surface 35 in cross-section FIG. 8, or alternatively, as a rounded, elliptical, convex surface 36 in cross-section FIG. 8A. As in the device of FIG. 1, the respective upper and outer sections of the device of FIG. 7 transform in shape from a circular section to a polygon and change in form through intermediate shoulder 33. A flat bottom on a device either of the form of FIG. 1 or its inverted alternative FIG. 7 has a tendency to fix the heel or ankle against the flat bed surface, while a rounded lower surface as shown in FIG. 8A used with either configuration allows more rolling and sliding movement. A device in the form of FIG. 4A or FIG. 8A is preferred as an elbow protector, while the determination whether a heel or ankle device should allow or restrain movement is made on patient preference, medical preferability, or stock availability of a particular device form.

A combined heel and ankle protector is shown in FIG. 9 in a perspective view and in FIG. 9A in cross-section with a foot 100 therein. The patient has a slight edema in the lower leg. The device shown is a left foot version and includes heel recess 10H and oppositely facing ankle recesses 10LA for the outer left ankle and 10ILA for the inside left ankle. Ankle protector sections 91 and 93 and heel protector section 92 are indicated. As shown, the ankle recesses differ in depth to adapt to the differing protrusion characteristics of the ankles on either side of the foot. This parameter is preferable insofar as the cushion and the recess therein should conform to the presenting physiology of the heel, ankle or elbow at which it is applied. in the device of FIGS. 9 and 9A, the cushion essentially cups the foot at the heel and ankle region of the foot, extending forward on the foot beyond the axis of the ankle about 6 cm in a medium adult size. The effect of the edema shown also illustrates that a preferred design for the protector at a body location where an extended cushion surface abuts the skin as a platform for the cushion, as at an ankle site, is that the edge of the recess smoothly conforms with the body surface with which it is in contact and should not include a sharp abutment such as an angled edge. Where, however, the cushion does not need a support platform resting on the skin, such as in a heel or elbow application, this design consideration is of lesser concern. Another factor is the extent of breakdown at the site. For treatment use in conjunction with a dressing, the device and dressing should be smoothly conforming to body contours. Combined heel and ankle protector cups are provided in pairs, as are shoes. However, a symmetrical unit that compromises exact anatomical correlations and that is useful with either foot is also suitable. Preferably, the thickness of the cushion material on the outer ankle is also greater to adapt to greater pressure encountered when a patient sleeps on his/her side. The cup protector need not extend the full length of the foot, however, it may also include a side extension extending to the first protruding bone adjacent the large toe.

Sizing of the devices conforms to standard definitions of small, medium or large, pediatric or adult, and is in accord with known physiological dimensions. An ankle protector for the outer left ankle of a 170 pound adult male was formed in the shape of FIG. 1 from Temper Foam having compression and density characteristics corresponding to those of the same adult's wheelchair seat cushion. The device included a maximum dimension of about 7.5 cm in width and an overall thickness of about 5.0 cm with a concave heel recess 1.25 cm in maximum depth tapering outward to 2.5 cm in diameter at the skin facing surface at the perimeter region of the ankle. The device was used with medication pads and gauze and sponge dressings, as well as by itself. The device was easier to position and appeared more durable and effective that the use, at the same site, of a topically applied 6 cm×6 cm Silastic® gel sheeting pad made by Dow Corning FRANCE S.A., Cat No. 9001-0001 or resting the patient's ankle on a pillow or an extended gel pad cushion. An advantage of the device is that it is secured at the location of the prominence to be protected.

As the various alternative shapes of the device are illustrated in the drawings, it is evident that the device is formed of two shapes that differ in size, shape, or both and that the shapes are joined by an intrinsic intermediate connecting section. The difference in shapes of the sections allows a care giver an ability to more easily grasp the device and also assists in its proper orientation with respect to the prominence (e.g., in FIGS. 1, 4 and 4A, element 5; in FIGS. 7, 8 and 8A, element 38). For grasping purposes, opposite parallel sides are preferred, hence, the preferred section shapes include a hexagon or octagon. A second group of preferred shapes include closed curvilinear shapes such as circular, elliptical or oval shapes. The first section and the upper section may be formed in essentially the same shape in cross-section (FIG. 4A), the first section may be larger (FIG. 1) or lesser (FIGS. 7, 8 and 8A) in cross-section area than the upper section. Although a resilient closed cell polyurethane foam is a convenient material from which the device may be formed, a water or silicon gel and an air enclosure are suitable alternatives. In any variation, the device may also include an additional recess, or the existing recess therein may be adapted to receive a medication pad for the treatment of a skin breakdown proximate the bony prominence and the device may also be provided with an intrinsic adhesive surface for attachment to the skin at the location of the prominence.

What is claimed is:

1. A cushioning protector for use in the prevention and treatment of pressure caused breakdowns of soft body tissue known as bedsores or dermal ulcers, the protector to be applied adjacent bony body prominences at heels, ankles and elbows and comprising a cushion formed from a pressure resilient material adapted to be positioned on the skin adjacent and facing the bony prominence at the heel, ankle or elbow, the cushion including:

a site applied pad for facing the skin and containing a recess therein formed in the thickness of the pad in a first thickness section of the pad on the side thereof facing the skin, the recess sized essentially to conform to the shape of the bony prominence, the pad on the side facing the skin abutting the skin adjacent the perimeter of the bony prominence and supporting the cushion such that the recess therein embraces the body tissue at the prominence and the prominence is protected from pressure by the material forming the cushion, the recess further including therein a treatment pad for a soft tissue breakdown, the first section extending upwardly in thickness from the side facing the skin to an upper section having a cross-section differing from that of the first thickness section, the first thickness section and the upper section being intrinsically joined by an intermediate section between the first thicknesssection and the upper section, the site applied pad facing the body skin being maintained in place adjacent the skin at the location of the bony prominence by one or more than one of a dressing tape, a sleeve and a sock.

2. The device of claim 1 including an adhesive on the surface of the site applied pad facing the skin in the area of the surface of the pad essentially surrounding the recess.

* * * * *